US00PP14148P39

(12) United States Plant Patent
Gonzalez

(10) Patent No.: US PP14,148 P3
(45) Date of Patent: Sep. 16, 2003

(54) PORTULACA PLANT NAMED 'KAKEGAWA CY6'

(75) Inventor: Javier Gonzalez, Salinas, CA (US)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 10/058,770

(22) Filed: Jan. 30, 2002

(65) Prior Publication Data

US 2003/0145361 P1 Jul. 31, 2003

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—Jondle & Associates P.C.

(57) ABSTRACT

Portulaca 'Kakegawa CY6' is a new variety of *Portulaca oleracea*. This plant has a vigorous, spreading plant growth which produces unique dark red flower with a red ring surrounding a yellow flower eye at the base of the of the flower petals.

1 Drawing Sheet

Genus and species: *Portulaca oleracea*.
Variety denomination: 'Kakegawa CY6'.

BACKGROUND OF THE NEW PLANT

This invention relates to a new and distinct cultivar of Portulaca plant, hereinafter referred to by the name 'Kakegawa CY6'. Portulaca 'Kakegawa CY6' is a new variety of *Portulaca oleracea*. The plant has a vigorous spreading growth habit and can be used as a groundcover. It can also be used in a potted or hanging basket presentation. The invention's flowers are a unique dark red flower with a red ring surrounding a yellow flower eye at the base of the flower petals. The flowers are single and measure approximately 5.0 centimeters in diameter when fully open. The plant performs well in hot and dry climates. The plant is very resistant to rain, heat and drought.

ORIGIN AND ASEXUAL REPRODUCTION

The new cultivar is propagated asexually from vegetative cuttings. The asexual reproduction establishes that the plant does in fact maintain the characteristics described in successive generations. 'Kakegawa CY6' has been reproduced by stem cuttings in Salinas, Calif., and all of the characteristics thereof have been determined to be firmly fixed.

'Kakegawa CY6' originated as a sport from the variety 'Summer Joy Wine red' (U.S. Plant Pat. No. 12,251). The inventor isolated the sport in October, 1999 in a greenhouse in Salinas, Calif. A single lateral stem was identified which exhibited a dark red flower with a red ring around a yellow eye. The parent variety possesses a dark red flower with a red center. The original sport was isolated and rooted in soiless plant media. Twenty vegetative cuttings were then made from the original plant after it grew to a suitable size. All twenty plants were identical for leaf shape, flower color and overall plant habit. Subsequent annual vegetative propagation of these plants over the next two years produced uniform plants with the same characteristics.

BRIEF DESCRIPTION OF DRAWINGS

The accompanying drawings serve by color photographic means to illustrate the new plant variety, 'Kakegawa CY6'. The colors are represented as true as possible using conventional photographic procedures.

DETAILED DESCRIPTION OF THE NEW VARIETY

Figure 1:
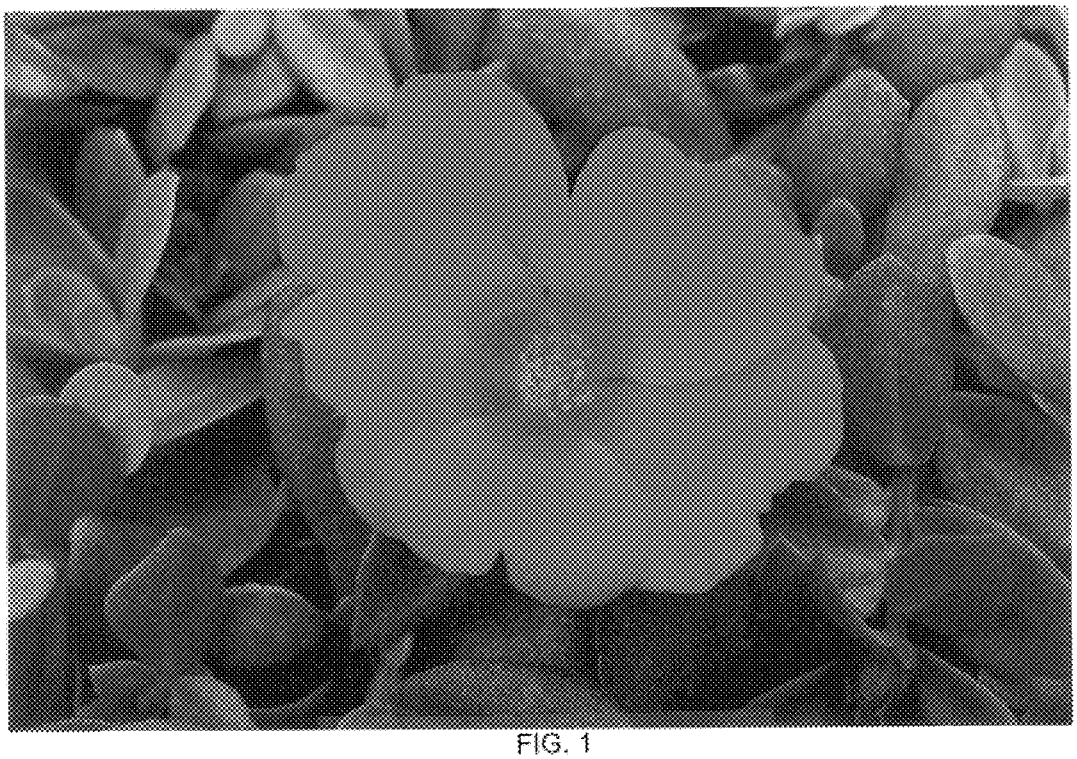
FIG. 1 is a close-up view of a 'Kakegawa CY6' flower illustrating its color and shape.
Figure 2:
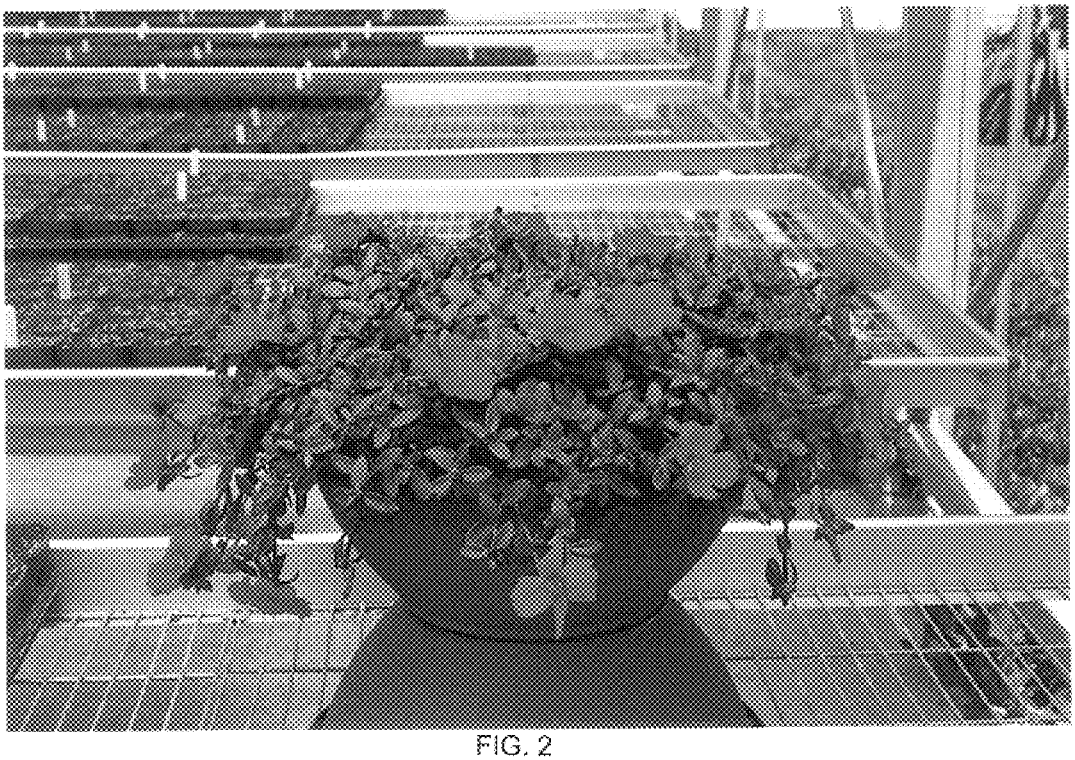
FIG. 2 is a view of several plants of the new cultivar growing in a 35.0 cm diameter pot.

The following description is based on observations and measurements from 14–16 week old plants grown in 15 cm pots at Salinas, Calif. Plants were propagated from vegetative cuttings and grown in a glass greenhouse. These plants were grown in plastic pots containing a peat moss-based medium. Soluble fertilizer containing 18% nitrogen, 8% phosphorus and 18% potassium were applied every fourth irrigation. The plants were typically watered twice per week. Pots were topdressed with a slow release fertilizer containing 18% nitrogen, 8% phosphorus and 18% potassium. The average air temperature was 24° C.

Color designations were made according to The Royal Horticultural Society Colour Chart published by The Royal Horticultural Society of London, England.

Origin: Japan
Parentage: A vegetative sport from variety 'Summer Joy Wine Red' (U.S. Plant Pat. No. 12,251).
Classification:
*Family.*—Portulacaceae.
*Genus.*—Portulaca.
*Species.*—*oleracea*.
*Commercial.*—Portulaca/Purslane 'Kakegawa CY6'.
Plant:
*Growt habit.*—Prostrate.
*Plant height.*—23.0 cm.
*Spread.*—85 cm (in a six-inch pot).

*Life cycle.*—Perennial.
*Time to produce a rooted cutting.*—2 weeks.
*Time to bloom from propagation.*—6–8 weeks.
*Time to produce a rooted cutting.*—Vegetative cuttings root in 7–10 days after sticking into a rooting medium like a peat moss based mix; the cuttings will form roots without the use of overhead mist.
*Flowering season/requirements.*—Flowers year round at temperatures of 24°–35° C.; day neutral light requirements.
*Temperature.*—Will not tolerate temperatures below 7° C.

Stem:
*Color.*—Yellowish green (144C).
*Anthocyanin.*—R.H.S. 178B (greyed-red).
*Pubescence.*—Glabrous.
*Stem description.*—Round, slightly rough with lateral ridges.
*Diameter.*—5.0 mm.
*Length of interode.*—3.0–3.5 cm.

Leaf:
*Apex.*—Acute.
*Base.*—Rounded.
*Arrangement.*—Alternate.
*Leaf color.*—Upper surface RHS 137C (green); lower surface RHS 138C (green).
*Anthocyanin.*—R.H.S. 58A (red-purple).
*Margin.*—Entire.
*Length* (*average*).—3.0 cm.
*Width* (*average*).—1.5 cm.
*Shape.*—Oblong.
*Thickness.*—1.0 mm.
*Texture.*—Smooth.
*Petiole color.*—RHS N144D (yellow-green).
*Petiole length.*—2.0 mm.
*Petiole diameter.*—2.0–3.0 mm.

Flower:
*Calyx.*—2 sepals; 1.0 cm×1.0 cm; free.
*Sepal shape.*—Eliptic.
*Sepal texture.*—Double lobed, slightly sinuate.
*Sepal apex shape.*—Cuspidate.
*Sepal color.*—R.H.S. 146D (yellow-green) in the center and lighter towards the margin until the tissue becomes transparent.
*Corolla.*—5 petals; free.
*Flower diameter.*—4.0–5.0 cm.
*Bud color.*—R.H.S. 138B (green).
*Bud shape.*—Round and pointed at the top.
*Bud surface.*—Shiny.
*Bud size.*—Length is 1.1–1.2 cm; diameter is 8 mm.
*Duration of flower life.*—One day.
*Flowering habit.*—Determinate.
*Placenta arrangement.*—Central.
*Inflorescence type.*—Solitary, sessile.
*Stamens.*—50; Filament color RHS 61B (red-purple) with a length of 6 mm; anther color R.H.S. 24A (orange).
*Pistil.*—1, branched on top with 5 branches.
*Stigma.*—RHS 61B (red-purple).
*Style.*—RHS 61B (red-purple) with a length of 1.0 cm.
*Petal size.*—3.0×2.8–3.0 cm (l×w).
*Petal shape.*—Double lobed; obovate.
*Petal margin.*—Double lobed; slightly sinuate.
*Petal apex.*—Retuse.
*Petal texture.*—Smooth and soft.
*Petal color.*—Upper surface RHS 61B (red-purple) at distal half and RHS 60A (red-purple) at basal half; lower surface RHS 61C (red-purple) at distal half and RHS 60A (red-purple at basal half; base of petal upper and lower surface R.H.S. 154A (yellow-green).
*Produces seed.*—No.
*Habit.*—The flowers bloom during midmorning and close at night. Each flower blooms only once and are produced throughout the growing season. The plants produce flowers regardless of day length; the plants are day neutral. Plants can have 40 to 50 open flowers at one time and have no fragrance.
*Hardiness.*—Plant is heat tolerant; thrives in heat and humidity; plant is not cold tolerant or below 7° C.

Disease and Insect Resistance

No unusual susceptibility to diseases or insects have been observed.

Comparison with Other Known Varieties

'Kakegawa CY6' is most similar to the variety Summer Joy Rose (U.S Plant Pat. No. 12,285) in that its petal color is darker red and the base of the petals and the anther create a yellow eye. 'Kakegawa CY6' and 'Summer Joy Rose' are similar in petal morphology (size, shape, texture, margin, and apex) and the two varieties have the same pollen color, R.H.S. 24A (orange). 'Kakegawa CY6' petals are slightly darker (RHS 61B, red-purple) than 'Summer Joy Rose' petals (R.H.S. 74A, red-purple), and the base of 'Kakegawa CY6' petal changes to a darker red (R.H.S. 60A, red-purple) near the base. The basal ⅛ inch of 'Kakegawa CY6' petals are yellow (R.H.S. 154A). The base of 'Summer Joy Rose' petals change to yellow (R.H.S. 12A) in the basal ¼ inch. At the margin of the two colors is streaking and fading of the two different colors.

We claim:

1. A new and distinct Portulaca plant as shown and described herein.

* * * * *